United States Patent
Childers

(10) Patent No.: US 7,481,213 B2
(45) Date of Patent: *Jan. 27, 2009

(54) MEDICAMENT DISPENSER

(75) Inventor: Winthrop D. Childers, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 716 days.

This patent is subject to a terminal disclaimer.

(21) Appl. No.: 10/777,448

(22) Filed: Feb. 11, 2004

(65) Prior Publication Data

US 2005/0172956 A1 Aug. 11, 2005

(51) Int. Cl.
*A61M 11/00* (2006.01)
*A61M 16/00* (2006.01)
*B05D 7/14* (2006.01)
*B65D 83/06* (2006.01)

(52) U.S. Cl. .............................. 128/200.23; 128/203.15

(58) Field of Classification Search ............ 128/200.23, 128/200.14, 200.16, 204.21, 203.12, 202.22, 128/205.23; 222/636; 239/338
See application file for complete search history.

(56) References Cited

U.S. PATENT DOCUMENTS

| | | | |
|---|---|---|---|
| 4,542,650 A | 9/1985 | Renken et al. |
| 4,776,214 A | 10/1988 | Moran et al. |
| 4,853,717 A | 8/1989 | Harmon et al. |
| 4,967,208 A | 10/1990 | Childers |
| 4,969,357 A | 11/1990 | Mickler |
| 5,035,138 A | 7/1991 | Abdel-Rahman |
| 5,103,244 A | 4/1992 | Gast et al. |
| 5,108,193 A | 4/1992 | Furubayashi |
| 5,115,250 A | 5/1992 | Harmon et al. |
| 5,209,111 A | 5/1993 | Agarwal et al. |
| 5,237,866 A | 8/1993 | Nijdam |
| 5,284,133 A | 2/1994 | Burns et al. |
| 5,331,953 A | 7/1994 | Andersson et al. |
| 5,363,842 A | 11/1994 | Mishelevich et al. |
| 5,372,040 A | 12/1994 | Hecht et al. |
| 5,404,871 A | 4/1995 | Goodman et al. |
| 5,415,029 A | 5/1995 | Uchiyama et al. |
| 5,450,336 A | 9/1995 | Rubsamen et al. |
| 5,469,750 A | 11/1995 | Lloyd et al. |
| 5,500,660 A | 3/1996 | Childers et al. |
| 5,511,415 A | 4/1996 | Nair et al. |
| 5,515,295 A | 5/1996 | Wang |
| 5,524,084 A | 6/1996 | Wang et al. |
| 5,563,638 A | 10/1996 | Osborne |
| 5,608,647 A | 3/1997 | Rubsamen et al. |
| 5,621,441 A | 4/1997 | Waschhauser et al. |
| 5,676,129 A | 10/1997 | Rocci, Jr. et al. |
| 5,692,492 A | 12/1997 | Bruna et al. |
| 5,721,257 A | 2/1998 | Baker et al. |

(Continued)

FOREIGN PATENT DOCUMENTS

EP 1 358 902 11/2003

(Continued)

*Primary Examiner*—Justine R Yu
*Assistant Examiner*—Kristen C Matter

(57) ABSTRACT

An inhaler that includes a fluid medicament supply, an ejector, an accumulator in fluid communication with the ejector, a valve that is in fluid communication with the fluid medicament supply and the accumulator, a sensor configured to sense an accumulator characteristic, and a controller configured to operate the valve in response to the accumulator characteristic.

19 Claims, 3 Drawing Sheets

U.S. PATENT DOCUMENTS

Figure 4A:
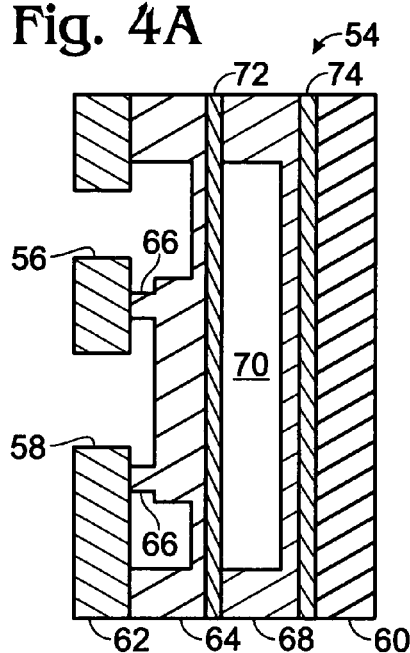

| | | | |
|---|---|---|---|
| 5,724,957 | A | 3/1998 | Rubsamen et al. |
| 5,726,357 | A | 3/1998 | Manaka |
| 5,780,736 | A | 7/1998 | Russell |
| 5,812,157 | A | 9/1998 | Nguyen et al. |
| 5,869,758 | A | 2/1999 | Huiberts |
| 5,880,748 | A | 3/1999 | Childers et al. |
| 5,881,716 | A | 3/1999 | Wirch et al. |
| 5,894,841 | A | 4/1999 | Voges |
| 5,925,021 | A | 7/1999 | Castellano et al. |
| 5,929,333 | A | 7/1999 | Nair |
| 5,952,571 | A | 9/1999 | Arai et al. |
| 5,992,990 | A | 11/1999 | Childers et al. |
| 6,029,659 | A | 2/2000 | O'Connor |
| 6,131,566 | A | 10/2000 | Ashurst et al. |
| 6,138,669 | A | 10/2000 | Rocci, Jr. et al. |
| 6,158,431 | A | 12/2000 | Poole |
| 6,162,443 | A | 12/2000 | Flament-Garcia et al. |
| 6,186,956 | B1 | 2/2001 | McNamee |
| 6,192,882 | B1 | 2/2001 | Gonda |
| 6,196,218 | B1 | 3/2001 | Voges |
| 6,220,243 | B1 | 4/2001 | Schaeffer et al. |
| 6,221,653 | B1 | 4/2001 | Caren et al. |
| 6,223,746 | B1 | 5/2001 | Jewett et al. |
| 6,224,897 | B1 | 5/2001 | Reitberg |
| 6,234,167 | B1 * | 5/2001 | Cox et al. ............... 128/200.14 |
| 6,257,690 | B1 | 7/2001 | Holstun |
| 6,280,012 | B1 | 8/2001 | Schloeman et al. |
| 6,325,475 | B1 | 12/2001 | Hayes et al. |
| 6,328,405 | B1 | 12/2001 | Weber et al. |
| 6,378,988 | B1 | 4/2002 | Taylor et al. |
| 6,390,453 | B1 | 5/2002 | Frederickson et al. |
| 6,443,146 | B1 | 9/2002 | Voges |
| 6,460,537 | B1 | 10/2002 | Bryant et al. |
| 6,629,456 | B2 | 10/2003 | Kohno |
| 6,830,046 | B2 * | 12/2004 | Blakley et al. ......... 128/200.14 |
| 2002/0077369 | A1 | 6/2002 | Noolandi |
| 2002/0109744 | A1 | 8/2002 | Shindo |
| 2002/0185125 | A1 | 12/2002 | Klimowicz et al. |
| 2003/0072717 | A1 | 4/2003 | Reinhold et al. |
| 2003/0101991 | A1 | 6/2003 | Trueba |
| 2004/0163641 | A1 * | 8/2004 | Tyvoll et al. ........... 128/200.23 |
| 2005/0051162 | A1 * | 3/2005 | Schuler et al. ......... 128/200.23 |
| 2005/0150489 | A1 * | 7/2005 | Dunfield et al. ........ 128/200.14 |

FOREIGN PATENT DOCUMENTS

| | | |
|---|---|---|
| EP | 1 452 199 | 9/2004 |
| WO | WO 2004/041340 | 5/2004 |

\* cited by examiner

Fig. 1
Fig. 2
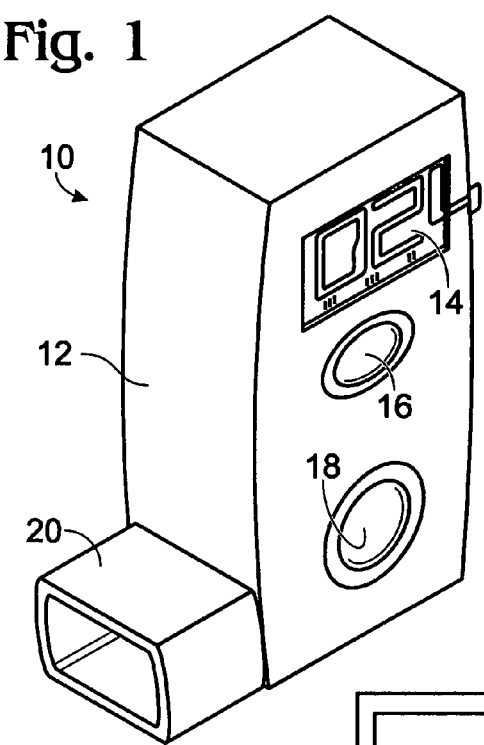
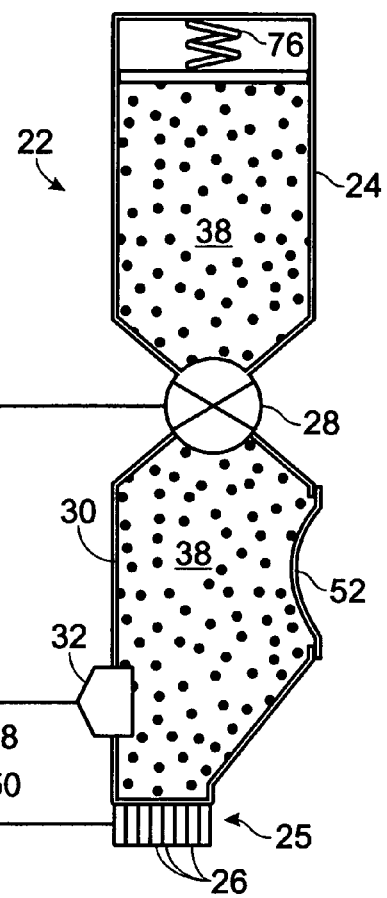
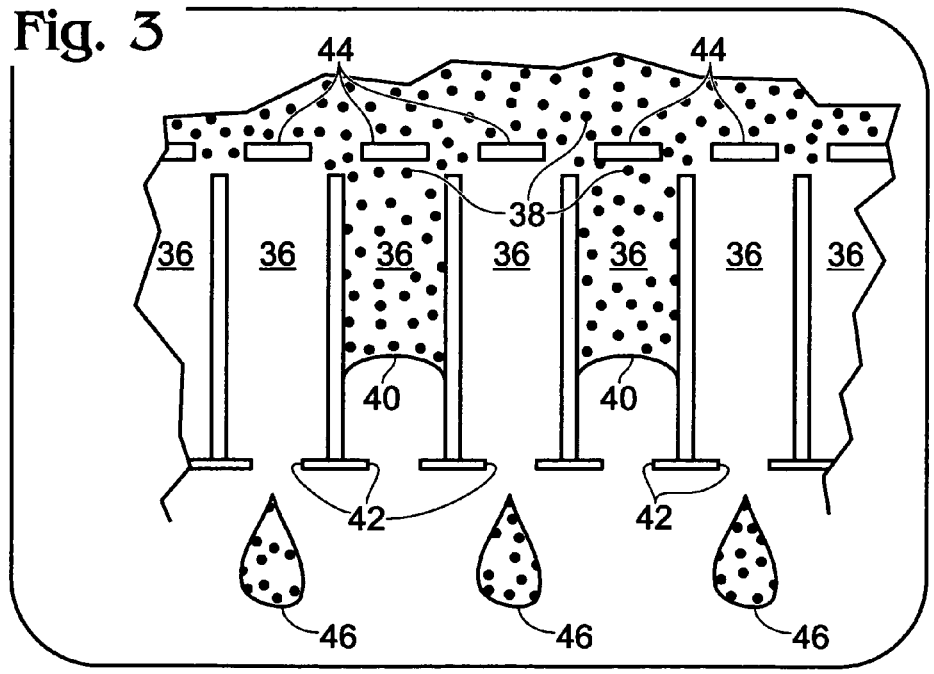
Fig. 3

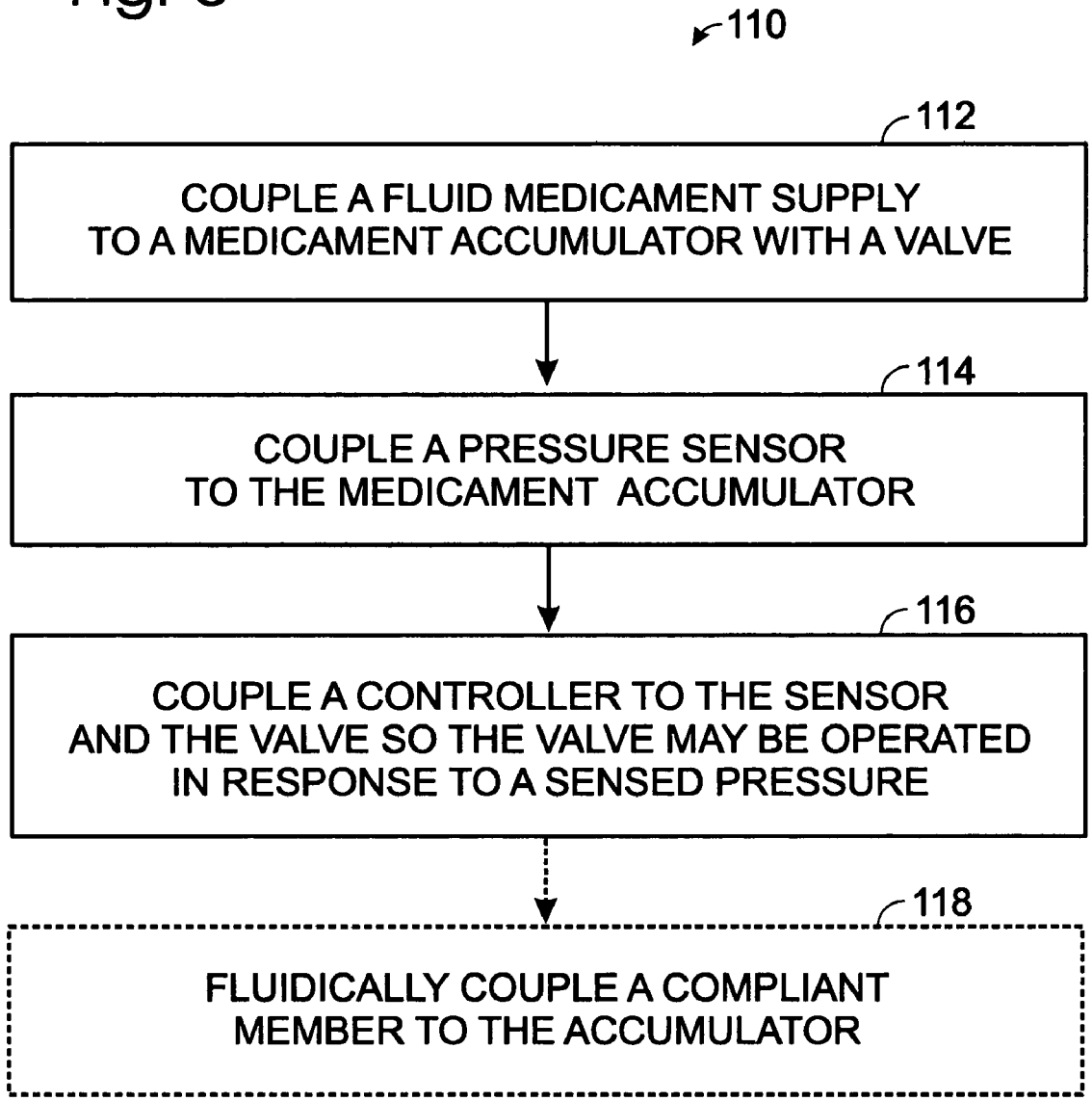

MEDICAMENT DISPENSER

BACKGROUND

Inhalers provide an alternative drug-delivery method that permits patients to aspirate medication rather than swallow a pill, or drink or inject medication. In some cases, such as with medications that directly target the patient's lungs, aspiration enables the medicine to reach the target area more quickly. In addition, aspiration is typically considered to be less painful than other drug-delivery methods.

Many inhalers rely upon mechanical atomizers or a pressurized cartridge to dispense medication. The dose delivery of such mechanisms can be dependent upon the force exerted on the activation mechanism, the pressure of carrier gas, and the inhalation force exerted by the user. As such, the dose delivery is generally imprecise, and such inhalers are typically only useful with medications having a broad dosage tolerance.

As an alternative, electronic inhalers, such as those that utilize bubble jet or piezoelectric ejectors to dispense medication, may offer a more advantageous method of dose delivery. However, a positive medication pressure may result in medication leaking from the ejector orifices of the inhaler. The inhaler may therefore keep the medication at a slight back or negative gauge pressure. However, too much back pressure may result in the ejectors of the inhaler being starved of medicament, and "deprimed". If the ejectors are deprimed in this way, the inhaler may subsequently misfire, resulting in inaccuracy in the ejected dose. Excessive back pressure may also cause air to be sucked into the inhaler when not in operation, causing air bubble entrapment that can lead to ejection problems and/or errors in dosage.

In addition, variations in the pressure of the medication supply used by the inhaler may still alter the dosage delivered over the lifetime of the supply. Variations in medication pressure may also effect the size of the individual droplets generated by the inhaler. Droplets that are too small may not be retained by the lungs, and may be exhaled out of the body instead. Similarly, droplets that are too large may not be absorbed by the lungs, and may also be exhaled out of the body.

BRIEF DESCRIPTION OF THE DRAWINGS

FIG. 1 depicts an inhaler according to an embodiment of the invention.

FIG. 2 is a semi-schematic depiction of the inhaler of FIG. 1.

FIG. 3 is a depiction of the ejectors of the inhaler of FIG. 1.

FIG. 4 is a semi-schematic depiction of an electronic valve, according to an embodiment of the invention. FIG. 4A shows the valve in a closed configuration. FIG. 4B shows the valve in an open configuration.

FIG. 5 is a flowchart for the operation of an inhaler, according to an embodiment of the invention.

FIG. 6 is a flowchart for a method of manufacturing an inhaler, according to an embodiment of the invention.

DETAILED DESCRIPTION

Referring initially to FIG. 1, an inhaler according to an embodiment of the present invention is shown at 10. Inhaler 10 includes a body 12 that may enclose the inhaler apparatus. As will be appreciated upon reading further, inhaler 10 may be configured to effect ejection of a selected dosage of medicament/inhalant from in response to a signal sent by a controller. Suitable medicaments include those typically found in liquid, solid, powder, paste or other forms.

Inhaler 10 may include a display 14 that is configured to provide information to the user of the inhaler, such as the number of doses administered and/or the number of doses remaining in the inhaler, or the dosage that will be provided by the inhaler upon activation. Display 14 may also be adapted to provide the user with information such as patient name, patient identification number, prescribing physician name, prescribing physician identification number, type of medication, recommended dosage, dose regimen, available alterations to the recommended dosage and/or dose regimen, etc. As will be appreciated, display 14 may be located in any convenient location on body 12.

The inhaler may include one or more input mechanisms, such as a depressible button 16, to permit the user to select the information to be displayed by display 14, or to modify the operating parameters of the inhaler. For example, pushing button 16 may permit the user to change the operator parameter currently displayed, and/or change the dosage delivered by the inhaler. Inhaler 10 may further include an actuator, such as a depressible button 18, that when triggered results in the ejection of a dose of medicament in a form appropriate for inhalation by the user via a mouthpiece 20. Button 18 could alternatively take the form of a trigger, switch, or touch-sensitive button, among others. Button 16 and/or button 18 may be located on the side of the inhaler body, as shown, or may be positioned in virtually any other location convenient to the user.

It will be appreciated that mouthpiece 20 may take alternative forms according to the particular medicament dispensed, the age of the user, and the medical treatment being implement, including for example forms which may be adapted to fit over a patient's mouth and/or nose. In addition, body 12 may be shaped to provide regions to accommodate the hand and/or fingers of the user. The present disclosure is not limited to the more traditional L-shaped inhaler, as shown in FIG. 1, but may also include linear inhaler designs, wherein the medicament supply is generally located along the same axis as the mouthpiece.

Inhaler 10 typically includes an ejection apparatus 22 for ejecting droplets of fluid medicament, as depicted semi-schematically in FIG. 2. The apparatus includes a fluid medicament supply 24, an ejector head 25 that includes a plurality of ejectors 26, a valve 28 that may be in fluid communication with the fluid medicament supply, an accumulator 30 that defines an accumulator volume that may be in fluid communication with the ejectors, a sensor 32 that may be configured to sense the pressure of the fluid within the accumulator, and a controller 34 that may be configured to operate the valve in response to the pressure within the accumulator.

The ejectors of the ejection apparatus serve to generate the medicament aerosol for inhalation by the user. As shown in greater detail in FIG. 3, each ejector may include an ejector chamber 36 that is in fluid communication with the fluid medicament accumulator 30. Fluid medicament 38 may pass from the accumulator into the ejector chamber itself. Each ejector may be adapted to receive and contain a charge of fluid medicament within the ejector chamber. This may be accomplished, in part, by the geometry of the ejector itself, which may lead to formation of a meniscus 40 within the ejector chamber adjacent an ejection orifice 42. Typically medicament does not pass through ejection orifices without en ejection event, due to the presence of such menisci.

Typically, each ejector includes at least one ejection element 44 configured to selectively and controllably eject medicament from within the corresponding ejector chamber as a vaporized medicament droplet 46. The ejection element (also referred to as a vaporization element) may take the form of a heating element opposite the ejection orifice. In this embodiment, in response to an ejection signal from controller 34 (e.g., a predetermined voltage applied across the heating element), the heating element may be activated, heating medicament in the vicinity of the heating element which, in turn, expands toward the ejection orifice, overcoming opposing forces of the meniscus and forcing medicament out of the ejection orifice in a predictably-sized droplet. The size and trajectory of such an ejected droplet may be reliably predicted based on the size and shape of the ejector and the ejector orifice, as well as the power dissipated in the chamber.

Once a vapor droplet has been ejected, and the ejection element deactivated (e.g. cooled), medicament may again flow into the ejector chamber, effectively filling it with a new charge of medicament upon formation of a meniscus adjacent the ejection orifice.

Ejection element 44 may take any of various forms, including for example, a resistor, a piezoelectric transducer, vibration of a porous membrane, or other ejector capable of independent activation by the inhaler's controller. In each case, the presently-described inhaler is typically able to produce an inhalant stream without the use of an aerosol carrier or propellant.

It should be appreciated that each ejection element may be controlled independently, in groupings, or in selected subsets of the full ejector set. By electronically controlling the rate of ejection element activation, it may be possible to control the rate of medicament ejection, and thus the medicament dosage produced by the inhaler. Dosage may also be regulated by an appropriate combination of firing rate and quantity control. Such regulation may be typically effected using controller 34. Controller 34 may be adapted to control inhaler 10 through electronic means, mechanical means, or both. Controller 34 thus may include a processor 48 and a memory 50 configured to store preprogrammed physician-selected, pharmacist-selected, and/or user-selected operating parameters. Memory 50 may include volatile memory, nonvolatile memory, or both. User inputs, such as those indicated at 16 and 18 typically communicate with controller 34, for example, to provide processor 48 with information/direction regarding the dosage of medicament to be released. Such information may be provided by the user, or may be provided by a physician or pharmacist either directly or indirectly.

Controller 34 may be in communication with ejectors 26 so as to provide control of ejection elements 44. Typically, such direction comes in the form of an electronic signal directed to one or more ejection elements to effect activation of such element(s), and thus, to effect ejection of droplets of medicament. Thus, when a user depresses or otherwise activates the activation input 18, controller 34 may send an appropriate ejection signal to at least one ejection element 44. Upon receipt of an ejection signal, each ejection element produces a droplet of medicament, as described above. Typically, the force of the expanding change of medicament within an associated ejection chamber may be sufficient to successfully eject the droplet of medicament from the ejection chamber. The duration, intensity, and/or other characteristic of the electronic signal may be altered to effect changes in the medicament dosage and/or ejection characteristic, depending on the type of ejection element used, and the dosage desired.

Inhaler 10 may further include a power supply (not shown). The power supply may be a battery or other suitable power supply, whether disposable or permanent. In some cases it may be desirable for the power supply to be a replenishable power supply, such as a rechargeable battery.

The medicament pressure within accumulator 30 may be at least partially regulated by fluidically coupling the medicament supply within the accumulator to a compliant member 52, as shown in FIG. 2. Compliant member 52 may be resilient and/or elastic, so that as the inhaler is activated, and medicament ejected from the ejection apparatus, and the pressure within the accumulator decreases, the compliant member 52 may, for example, deform elastically into the accumulator. This compliance serves to regulate the back pressure within the accumulator. Alternatively, where the regulated pressure is a positive pressure, the compliant member may be deformed elastically during charging of the accumulator from the medicament supply, such that the compliant member relaxes as the pressure decreases.

The resilience of the compliant member may be provided by a spring bag, a rubber bladder, a diaphragm, or other suitable mechanism without departing from the scope of this overall concept. The compliant member may not be required to be a discrete component of the inhaler. For example, the accumulator itself may function as a compliant member, in that medicament may be ejected from the inhaler at least once before the pressure change within the accumulator mandated refreshing the medicament supply within the accumulator. Similarly, the accumulator itself may be manufactured from a sufficiently resilient material that the body of the accumulator itself serves to regulate the pressure within the accumulator. As indicated above, where the ejection mechanism used in ejection apparatus 22 may perform satisfactorily under positive fluid pressure, the compliant member may be configured to provide a regulated positive pressure within the accumulator, rather than a negative back pressure.

By regulating the medicament pressure at the ejector, the operation parameters of the inhaler may be rendered relatively insensitive to the orientation of the inhaler itself. That is, the inhaler may operate efficiently even when held at an angle. In addition, by monitoring fluid pressure within the accumulator, the inhaler controller may be further configured to permit detection of low medicament levels, and therefore disable operation of the inhaler before the adverse effects of operation without medicament can occur.

The action of the compliant member may assist in eliminating short-term surges (or 'spikes') in medicament pressure, and therefore may help regulate the fluid being delivered to the ejectors. In one embodiment, the compliant member takes the form of a resilient diaphragm separating the outside atmosphere from the medicament fluid contained within the accumulator. Such a diaphragm is typically selected so that the size and resilience of the diaphragm itself results in an operating pressure range that permits the inhaler to deliver at least one dose of medicament from the fluid within the accumulator without replenishing the fluid within the accumulator from the fluid supply via valve 28.

The accumulator volume may be fluidically coupled to the outlet of a controllable valve mechanism 28, that opens and closes in response to the measured pressure within accumulator 30. Any valve that permits the regulated and controlled addition of medicament fluid to the accumulator volume from the medicament supply may be an appropriate valve for the purposes of this disclosure. A variety of such controllable valve mechanisms are commercially available and selection of a particular design for a specific implementation would be within the purview of a person skilled in the art. For example, appropriate valve mechanisms may include can be a peristaltic valves ("pinch valves"), solenoid valves, or any other valve that can be actuated automatically.

It should be appreciated that while the valve mechanism may be such that the controllable valve mechanism 28 is either open or closed, it should be appreciated that more costly valve mechanisms with variable flow control can be substituted for an "on/off" valve mechanism.

The inlet of valve 28 may be fluidically coupled to fluid medicament supply 24. When the backpressure in the accumulator reaches a minimum acceptable value, valve 28 may be opened, fluidically connecting the accumulator volume to the fluid medicament supply. Fluid medicament may then flow into the accumulator, increasing the medicament pressure. When the backpressure is greater than a second, acceptable value, the valve may close. In this way, valve 28 and compliant member 52 may act as an active pressure regulation mechanism. Typically, the fluid within accumulator 30 may be maintained at a pressure that varies within the operational limits of ejectors 26, regardless of the pressure within the fluid medicament supply.

Figure 4B:
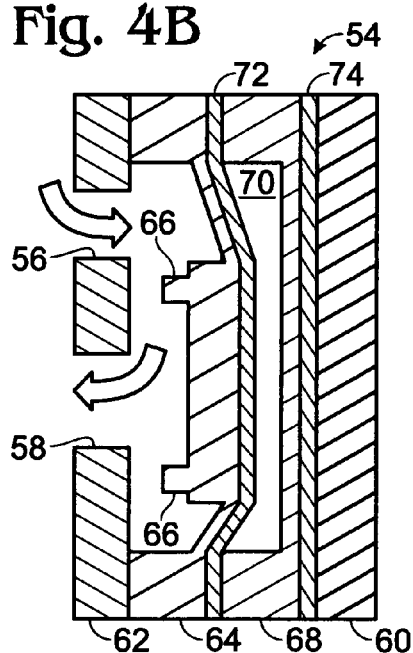

Valve 28 may be an electronically controlled valve. In particular, small solenoid activated fluid valves are appropriate valves for use in the disclosed inhaler. If a smaller valve with reduced power requirements would be desirable, any of a variety of fabricated microvalves may be useful. By microvalve is meant a mechanical device that controls the flow of fluid in a highly compact or a microscopic channel. Microvalves may be actuated by applied electrostatic force, magnetic force, or piezoelectric forces. Microvalves may be formed, for example, by thin film deposition, microlithography, micromachining, or a combination thereof. A representative microvalve 54 is depicted schematically in FIGS. 4A and 4B. Valve 54 includes valve inlet 56, a valve outlet 58, a fixed top plate 60, a fixed ground plate 62, and a flexible boss plate 64 that includes a valve seal 66. The flexible boss plate may be separated from the top plate by an isolating element 68 and a narrow air gap 70. Normally, the boss plate may be held firmly against the fixed group plate, so that valve seal 66 prevents fluid from flowing from valve inlet 56 to valve outlet 58. However, when a potential is applied between electrode 72 that is connected to the boss plate and electrode 74 connected to the fixed top plate, the boss plate may be electrostatically flexed, as shown in FIG. 4B. As a result, the seal may be lifted away from the fixed ground plate, and fluid may be permitted to flow from the valve inlet to the valve outlet.

The inhaler may include a sensor 32 that may be positioned to measure a characteristic of the accumulator. The sensor may be configured to measure the pressure of the medicament fluid within the accumulator directly, or may be configured to measure the volume defined by the accumulator and compliant member, and thereby measure the pressure of the medicament fluid indirectly. The sensor may communicate measurements to controller 34, so that valve 28 may be operated when needed. In one embodiment, the sensor is a pressure sensor that is disposed adjacent to the ejector head 25, so that the fluid pressure measured by the sensor closely corresponds to the fluid pressure at the ejectors. This may help ensure that the regulated fluid pressure at the ejectors may lie within the operational parameters stored in the controller. The fluid pressure may be sensed continuously, sensed at discrete intervals, or sensed in response to specified actions of the controller or of the user.

The fluid medicament supply may be integrated with the accumulator and the ejectors, or may be separately removable. In particular, it may be useful to utilize a fluid medicament supply that may be removed and replaced, for example, when refilling a prescription. It may be useful if the design of the fluid medicament supply was fluidically efficient. That is, the supply may be emptied substantially completely, leaving very little fluid medicament in the supply once low pressure render the inhaler unusable. Such considerations may optimize the safety, disposability, and cost of the inhaler itself. For example, pressurization of fluid medicament supply 24 may greatly improve the volumetric efficiency of the inhaler, by increasing the percentage of medicament that may be extracted from medicament supply 24. Pressurization may reduce stranded fluid volume to below 20%, below 10%, or even below 5% of the initial fluid volume in the fluid medicament supply. This may be an important consideration where the medicament formulation is costly, as a small amount of stranded fluid may be worth more than the entire inhaler mechanism. In addition, some countries may regulate the disposal of empty fluid containers having more than a certain amount of stranded fluid.

For these reasons, the fluid supply may include a pressurizing element 76, so that the fluid medicament supply may be pressurized. Pressurization of the fluid supply may ensure that sufficient fluid may be provided to the fluid valve upon demand to efficiently fill the accumulator volume. The fluid supply may be pressurized using a variety of methods. The fluid supply may include a pressurizing gas, or it may include a spring-loaded collapsible reservoir (as depicted in FIG. 2), or a gas pressurized elastomer or rolling diaphragm bag. Where the fluid supply includes a rolling diaphragm bag, it may be useful to utilize a flat spring, or 'constant force' spring, so that the pressure applied to the bag may be held substantially constant as the bag empties. Although a variety of pressurized fluid supplies have been discussed, it should be appreciated that a fluid medicament supply that permits the fluid to be actively pumped, or to flow gravimetrically into the accumulator may also be useful for the purposes of the disclosure.

Figure 5:
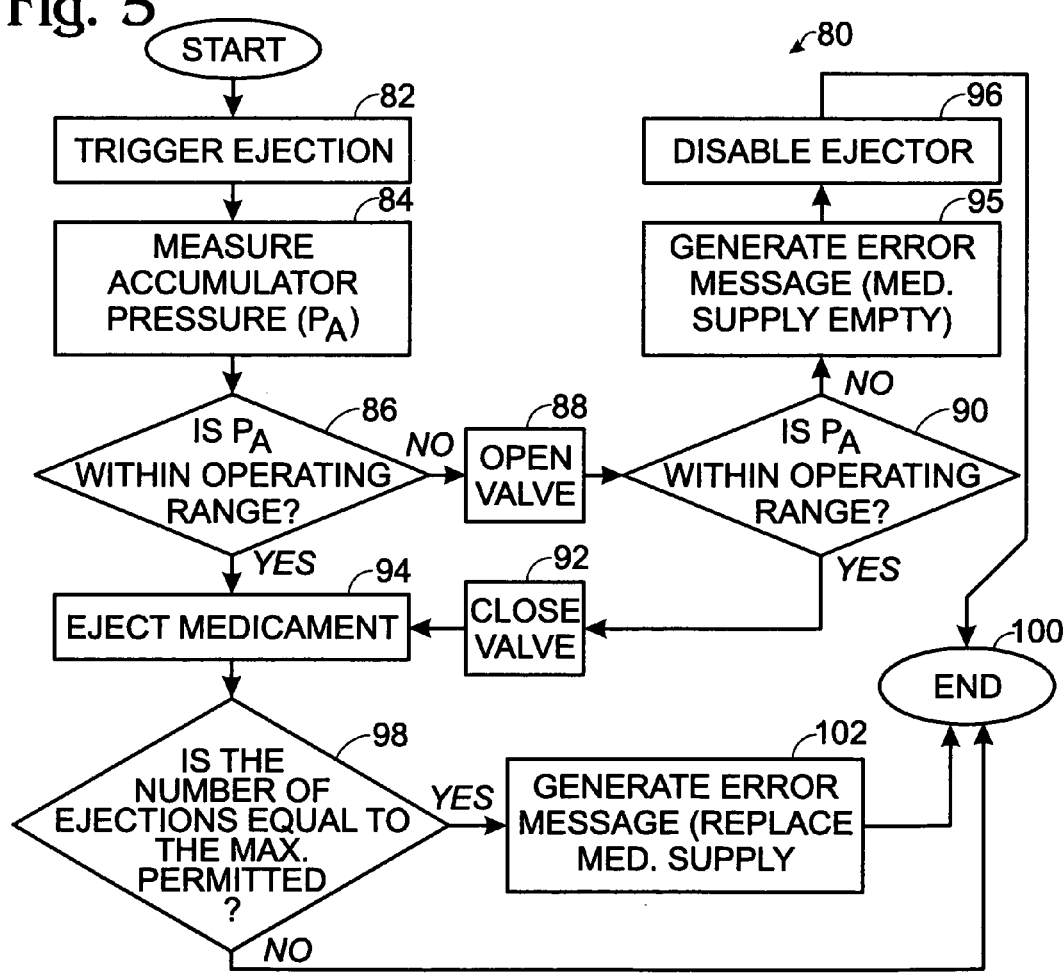

The operation of the disclosed inhaler may include steps such as are set out in flow chart 80 of FIG. 5. The user may trigger an ejection of medicament, at 82. The controller may then measure the fluid pressure within the accumulator using the pressure sensor, at 84. The controller may determine if the measured accumulator pressure lies within the pressure parameters recorded in the controller memory, at 86. If the measured accumulator pressure lies below the minimum value for operation of the ejectors, the valve to the medicament supply may be opened, at 88. In one embodiment, the valve may remain open until the accumulator pressure reaches a defined value within the operation range for the inhaler, at 90. Once an appropriate pressure is measured, the valve may be closed, at 92, and the medicament ejected, at 94. Where the valve may be open, and the pressure may fail to reach a defined minimum accumulator pressure after a set period of time, an error message may be generated that informs the user that the medicament supply may be empty, at 95. To prevent damage to the inhaler, the ejector mechanism may then be disabled, at 96. After an ejection event occurs, the controller may determine whether the total number of ejections performed using the medicament supply is equal or greater than the maximum number permitted for the medicament supply used, at 98. If the number of ejections is less than the maximum number permitted, the ejection process may be complete, at 100. If the number of ejections is equal or greater than the maximum number permitted for the medicament supply, the inhaler may then generate an error message for the user to replace the medicament supply, at 102.

It should be appreciated that rather than opening the valve, at 88, and then measuring the accumulator pressure until it lies within the operating range, the valve may be opened for a set time period, then closed, and the accumulator pressure measured. If the sensed accumulator pressure does not lie within the defined operating range, the valve may be opened for an additional defined period of time. Typically, if the measured pressure lies below a predefined first pressure, then the valve may be opened to permit additional fluid medicament to flow into the accumulator, and the accumulator pressure may be sensed again to determine when the accumulator pressure rises to at least a predefined second pressure.

The pressure-regulating inhaler disclosed herein may be manufactured according to the flowchart 110 set out in FIG. 6. The method may include coupling the fluid medicament supply to a medicament accumulator with a valve, at 112, coupling a pressure sensor to the medicament accumulator, at 114, and coupling a controller to the sensor and the valve, so that valve may be operated in response to a sensed pressure, at 116. The method may further include fluidically coupling a compliant member to the accumulator, at 118.

While various alternative embodiments and arrangements of an inhaler, and methods of using an inhaler have been shown and described above, it will be appreciated by those of skill in the art that numerous other embodiments, arrangements, and modifications are possible and are within the scope of the present disclosure. Those skilled in the art thus will understand that many variations may be made therein without departing from the spirit and scope as defined in the following claims. The present description should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application.

What is claimed is:

1. A medicament dispenser, comprising:
   a fluid medicament supply;
   an ejector;
   an accumulator for storing medicament in fluid communication with the ejector;
   a valve in fluid communication with the fluid medicament supply and the accumulator;
   a sensor configured to sense an accumulator characteristic; and
   a controller configured to operate the valve in response to the accumulator characteristic; and
   a compliant member that regulates pressure within the accumulator, wherein the compliant member is a resilient member.

2. The dispenser of claim 1, where the sensor is configured to sense fluid pressure within the accumulator.

3. The dispenser of claim 1, where the sensor is configured to sense a volume defined by the accumulator.

4. The dispenser of claim 1, wherein the sensor is fluidically coupled to the accumulator.

5. The dispenser of claim 4, wherein the sensor is configured to sense pressure adjacent the ejector.

6. The dispenser of claim 5, wherein the controller is configured to operate the valve to increase the pressure adjacent the ejector.

7. The dispenser of claim 1, wherein the compliant member is configured to regulate pressure by deforming elastically in response to changes in accumulator pressure.

8. The dispenser of claim 7, wherein the compliant member is configured to regulate negative accumulator pressure.

9. The dispenser of claim 7, wherein the sensor is coupled to the compliant member to sense the accumulator volume.

10. The dispenser of claim 1, wherein the valve includes a microvalve.

11. The dispenser of claim 10, wherein the microvalve includes an electrostatic actuator, a magnetic actuator, or a piezoelectric actuator.

12. The dispenser of claim 1, further comprising a display configured to provide information to a user of the dispenser.

13. The dispenser of claim 12, wherein the information includes the number of doses of medicament remaining in the dispenser.

14. The dispenser of claim 12, wherein the information includes an indication to replace the fluid medicament supply.

15. A method of dispensing a medicament using a medicament dispenser including a fluid medicament supply, an ejector, an accumulator for storing medicament in fluid communication with the ejector, a valve in fluid communication with the fluid medicament supply and the accumulator, a sensor configured to sense an accumulator characteristic, and a controller configured to operate the valve in response to the accumulator characteristic, the method comprising:
   sensing a medicament pressure within the accumulator;
   recharging the accumulator from the fluid medicament supply where recharging the accumulator includes opening a valve between the fluid medicament supply and the accumulator, where recharging the accumulator relaxes a compliant member that is fluidically coupled to the accumulator; and
   ejecting medicament from the accumulator.

16. A method of dispensing a medicament using a medicament dispenser including a fluid medicament supply, an ejector, an accumulator for storing medicament in fluid communication with the ejector, a valve in fluid communication with the fluid medicament supply and the accumulator, a sensor configured to sense an accumulator characteristic, and a controller configured to operate the valve in response to the accumulator characteristic, the method comprising:
   sensing a medicament pressure within the accumulator;
   recharging the accumulator from the fluid medicament supply where recharging the accumulator includes opening a valve between the fluid medicament supply and the accumulator, where recharging the accumulator flexes a compliant member that is fluidically coupled to the accumulator; and
   ejecting medicament from the accumulator.

17. The method of claim 16, further comprising comparing the sensed pressure to a minimum acceptable medicament pressure within the accumulator.

18. The method of claim 17, further comprising sensing a second medicament pressure within the accumulator and comparing the second pressure to a desired pressure.

19. The method of claim 18, where the second pressure is less than the desired pressure, further comprising generating a notification that the fluid medicament supply should be renewed.

* * * * *